(12) United States Patent
Strnad

(10) Patent No.: US 12,274,193 B2
(45) Date of Patent: Apr. 15, 2025

(54) SYSTEMS, APPARATUSES, AND METHODS FOR MONITORING SOIL CHARACTERISTICS AND DETERMINING SOIL COLOR

(71) Applicant: Precision Planting LLC, Tremont, IL (US)

(72) Inventor: Michael Strnad, Delavan, IL (US)

(73) Assignee: Precision Planting LLC, Tremont, IL (US)

(*) Notice: Subject to any disclaimer, the term of this patent is extended or adjusted under 35 U.S.C. 154(b) by 925 days.

(21) Appl. No.: 17/425,859

(22) PCT Filed: Jan. 29, 2020

(86) PCT No.: PCT/IB2020/050699
§ 371 (c)(1),
(2) Date: Jul. 26, 2021

(87) PCT Pub. No.: WO2020/161566
PCT Pub. Date: Aug. 13, 2020

(65) Prior Publication Data
US 2022/0000007 A1    Jan. 6, 2022

Related U.S. Application Data

(60) Provisional application No. 62/800,950, filed on Feb. 4, 2019.

(51) Int. Cl.
*A01B 79/00* (2006.01)
*A01B 79/02* (2006.01)
(Continued)

(52) U.S. Cl.
CPC ............ *A01B 79/005* (2013.01); *A01B 79/02* (2013.01); *A01C 7/203* (2013.01); *G01N 21/31* (2013.01);
(Continued)

(58) Field of Classification Search
USPC .......................................................... 702/189
See application file for complete search history.

(56) References Cited

U.S. PATENT DOCUMENTS

| | | |
|---|---|---|
| 5,999,650 A | 12/1999 | Ligon |
| 9,585,307 B2 | 3/2017 | Holland |
| (Continued) | | |

FOREIGN PATENT DOCUMENTS

| | | |
|---|---|---|
| CN | 106404682 A | 2/2017 |
| CN | 106846295 A | 6/2017 |
| (Continued) | | |

OTHER PUBLICATIONS

European Patent Office, Inernational Search Report for related International Application No. PCT/IB2020/050699, mail date Apr. 8, 2020.

(Continued)

*Primary Examiner* — Paul D Lee

(57) ABSTRACT

Systems, apparatuses, and methods for agricultural monitoring of soil characteristics and determining soil color are described herein. In one example, a method of calculating soil color data includes obtaining, with sensors of a soil apparatus, soil measurements. The method further includes calculating soil color values in a visible spectrum including at least one of red, green, and blue color values based on the soil measurements and determining color data for at least one color image without false image artifacts based on the calculated soil color values and associated coordinates within an agricultural field.

20 Claims, 14 Drawing Sheets

(51) Int. Cl.
  *A01C 7/20*   (2006.01)
  *G01N 21/31*  (2006.01)
  *G01N 33/24*  (2006.01)
  *A01C 5/06*       (2006.01)
  *A01C 7/10*       (2006.01)
  *A01C 21/00*      (2006.01)

(52) U.S. Cl.
  CPC .............. *G01N 33/24* (2013.01); *A01C 5/064* (2013.01); *A01C 7/102* (2013.01); *A01C 21/007* (2013.01); *G01N 33/245* (2024.05)

(56) References Cited

U.S. PATENT DOCUMENTS

| | | | |
|---|---|---|---|
| 2006/0158652 A1 | 7/2006 | Rooney et al. | |
| 2007/0208510 A1* | 9/2007 | Anderson | E02B 11/00 405/36 |
| 2017/0049044 A1* | 2/2017 | Stoller | A01C 7/201 |
| 2018/0125000 A1 | 5/2018 | Levy et al. | |
| 2018/0168094 A1 | 6/2018 | Koch et al. | |
| 2018/0184581 A1* | 7/2018 | Morgan | G01N 21/359 |
| 2020/0022301 A1* | 1/2020 | Ritland | A01C 7/206 |

FOREIGN PATENT DOCUMENTS

| | | |
|---|---|---|
| WO | 2007105312 A1 | 9/2007 |
| WO | 2014153157 A1 | 9/2014 |
| WO | 2015171908 A1 | 11/2015 |
| WO | 2018/061255 A1 | 4/2018 |
| WO | 2019070617 A1 | 4/2019 |
| WO | 2020161566 A1 | 8/2020 |

OTHER PUBLICATIONS

Chen et al., Photo-optical sensor system for rapid evaluation of planter seed spacing uniformity, found at https://www.spiedigitallibrary.org/conference-proceedings-of-spie?SSO=1, accessed Apr. 29, 2021.

* cited by examiner

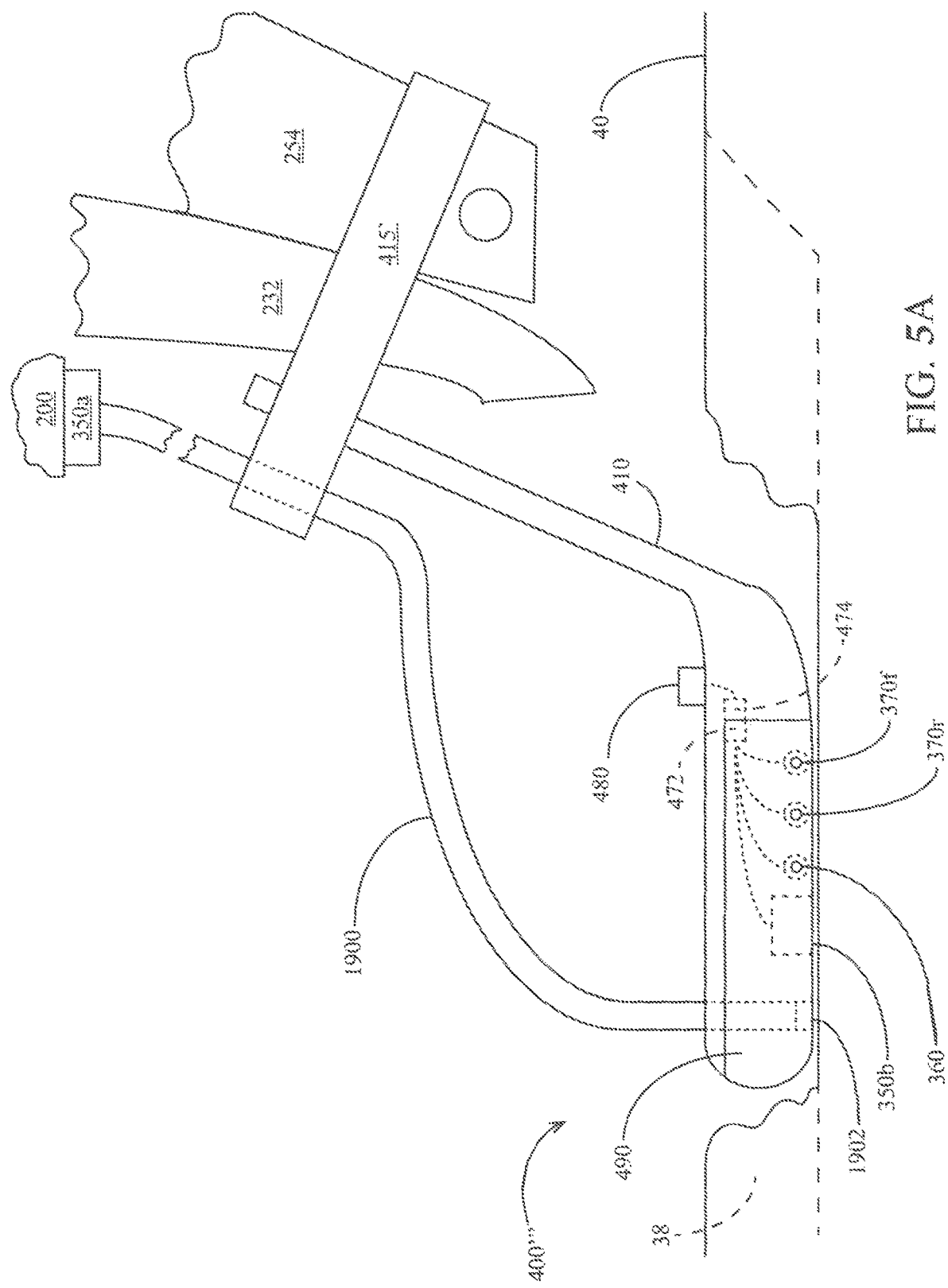

SYSTEMS, APPARATUSES, AND METHODS FOR MONITORING SOIL CHARACTERISTICS AND DETERMINING SOIL COLOR

CROSS REFERENCE TO RELATED APPLICATIONS

This application claims priority to U.S. Provisional Application No. 62/800,950, filed on 4 Feb. 2019, the entire contents of which are hereby incorporated by reference. This application is related to International Application No. PCT/US18/53832, filed on Oct. 2, 2018 entitled: SYSTEMS AND APPARATUSES FOR SOIL AND SEED MONITORING, the entire contents of which are hereby incorporated by reference.

TECHNICAL FIELD

Embodiments of the present disclosure relate to systems, apparatuses, and methods for agricultural monitoring of soil characteristics and determining soil color.

BACKGROUND

In recent years, the availability of advanced location-specific agricultural application and measurement systems (used in so-called "precision farming" practices) has increased grower interest in determining spatial variations in soil properties and in varying input application variables (e.g., planting depth) in light of such variations. However, the available mechanisms for measuring properties such as temperature are either not effectively locally made throughout the field or are not made at the same time as an input (e.g. planting) operation.

BRIEF DESCRIPTION OF THE DRAWINGS

The present disclosure is illustrated by way of example, and not by way of limitation, in the figures of the accompanying drawings and in which:

FIG. 5A illustrates another embodiment of the seed firmer 400''' that incorporates a fiber-optic cable 1900.

BRIEF SUMMARY

Systems, apparatuses, and methods for agricultural monitoring of soil characteristics and determining soil color are described herein. In one example, a method of calculating soil color data includes obtaining, with sensors of a soil apparatus, soil measurements including at least one of measurements for moisture, organic matter, porosity, type of soil, and furrow residue. The method further includes calculating soil color values in a visible spectrum including at least one of red, green, and blue color values based on the soil measurements and determining color data for at least one color image without false image artifacts based on the calculated soil color values and associated coordinates within an agricultural field. Currently, satellite imagery can give some information regarding soil zones based on observed soil color variation; however, those images can be distorted due to lighting, topography, shadows, weather, season, vegetation coverage, etc. . . . . The proposed method of capturing and representing the true soil color just below the surface is immune to most of the things that can distort satellite or aerial imagery. This will provide a true color image of the soil below the surface, typically at planting depth, un-distorted by the effects listed previously.

DETAILED DESCRIPTION

All references cited herein are incorporated herein in their entireties. If there is a conflict between a definition herein and in an incorporated reference, the definition herein shall control.

The terms trench and furrow are used interchangeably throughout this specification.

Depth Control and Soil Monitoring Systems

Figure 1:
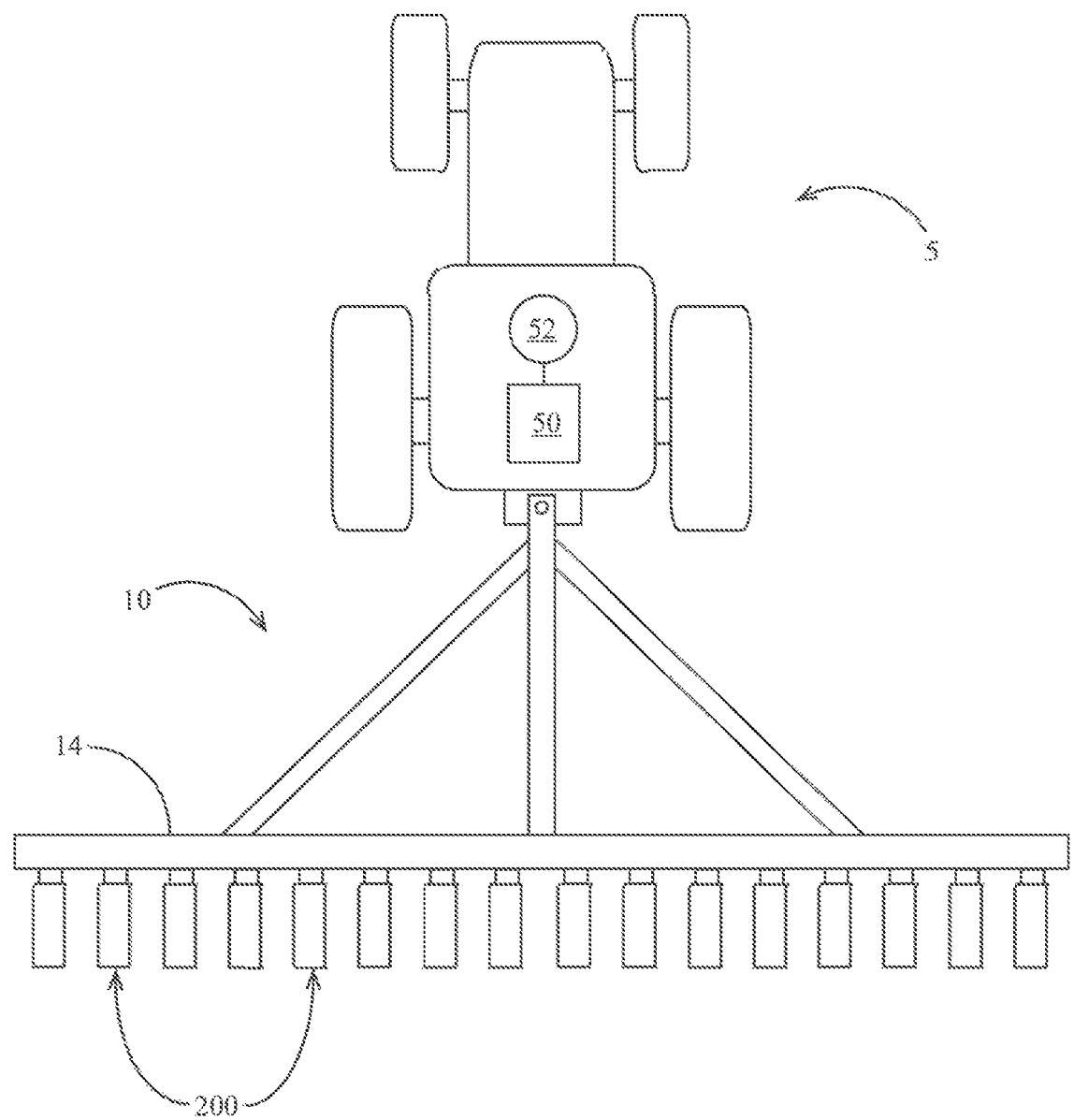
FIG. 1 is a top view of an embodiment of an agricultural planter.

Referring now to the drawings, wherein like reference numerals designate identical or corresponding parts throughout the several views, FIG. 1 illustrates a tractor 5 drawing an agricultural implement, e.g., a planter 10, comprising a toolbar 14 operatively supporting multiple row units 200. An implement monitor 50 preferably including a central processing unit ("CPU"), memory and graphical user interface ("GUI") (e.g., a touch-screen interface) is preferably located in the cab of the tractor 5. A global positioning system ("GPS") receiver 52 is preferably mounted to the tractor 5.

Figure 2:
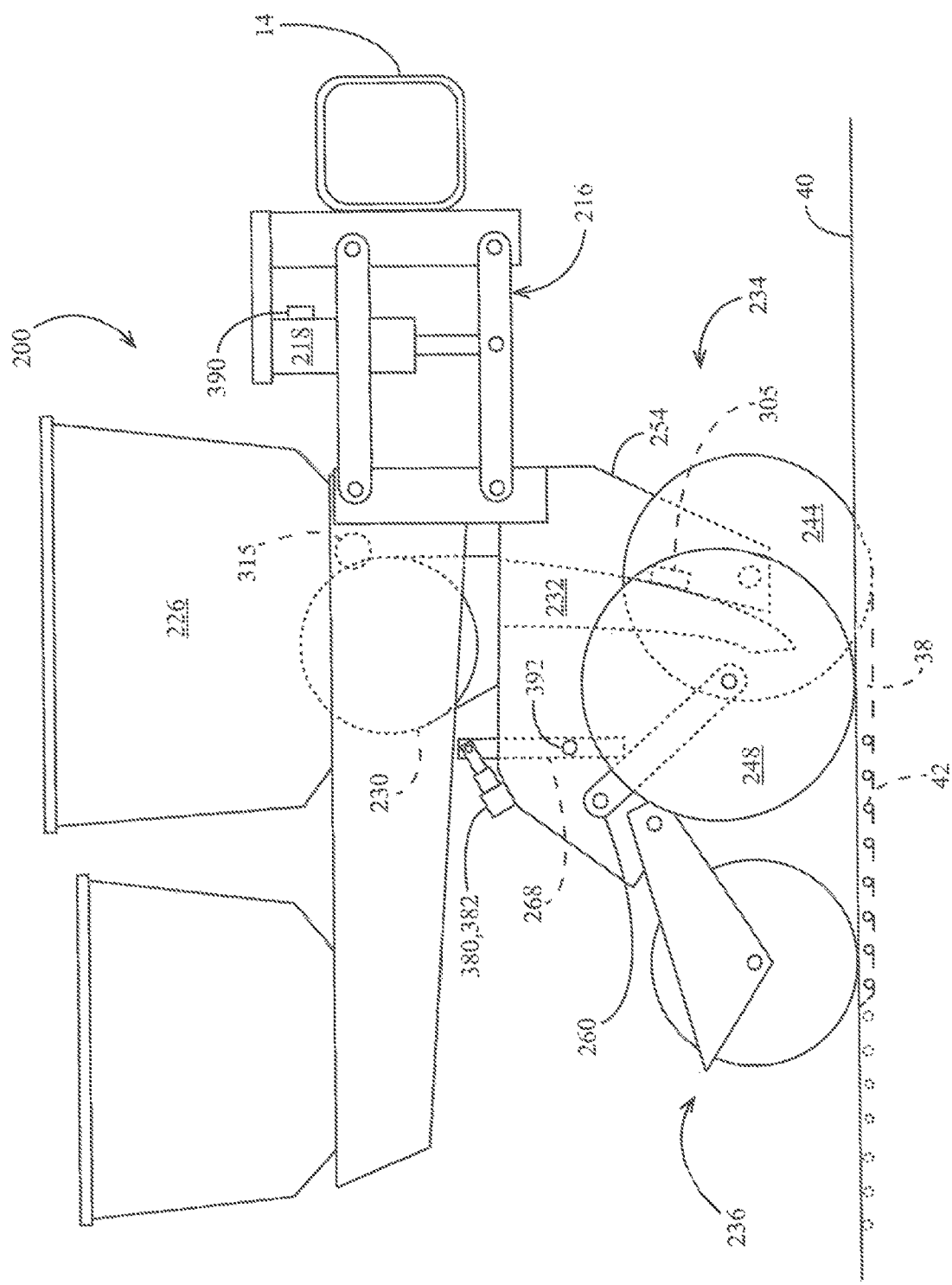
FIG. 2 is a side elevation view of an embodiment of a planter row unit.

Turning to FIG. 2, an embodiment is illustrated in which the row unit 200 is a planter row unit. The row unit 200 is preferably pivotally connected to the toolbar 14 by a parallel linkage 216. An actuator 218 is preferably disposed to apply lift and/or downforce on the row unit 200. A solenoid valve 390 is preferably in fluid communication with the actuator 218 for modifying the lift and/or downforce applied by the actuator. An opening system 234 preferably includes two opening discs 244 rollingly mounted to a downwardly-extending shank 254 and disposed to open a v-shaped trench 38 in the soil 40. A pair of gauge wheels 248 is pivotally supported by a pair of corresponding gauge wheel arms 260; the height of the gauge wheels 248 relative to the opener discs 244 sets the depth of the trench 38. A depth adjustment rocker 268 limits the upward travel of the gauge wheel arms 260 and thus the upward travel of the gauge wheels 248. A depth adjustment actuator 380 is preferably configured to modify a position of the depth adjustment rocker 268 and thus the height of the gauge wheels 248. The actuator 380 is preferably a linear actuator mounted to the row unit 200 and pivotally coupled to an upper end of the rocker 268. In some embodiments the depth adjustment actuator 380 comprises a device such as that disclosed in International Patent Application No. PCT/US2012/035585 ("the '585 application") or International Patent Application Nos. PCT/US2017/018269 or PCT/US2017/018274. An encoder 382 is preferably configured to generate a signal related to the linear extension of the actuator 380; it should be appreciated that the linear extension of the actuator 380 is related to the depth of the trench 38 when the gauge wheel arms 260 are in contact with the rocker 268. A downforce sensor 392 is preferably configured to generate a signal related to the amount of force imposed by the gauge wheels 248 on the soil 40; in some embodiments the downforce sensor 392 comprises an instrumented pin about which the rocker 268 is pivotally coupled to the row unit 200, such as those instrumented pins disclosed in Applicant's U.S. patent application Ser. No. 12/522,253 (Pub. No. US 2010/0180695).

Continuing to refer to FIG. 2, a seed meter 230 such as that disclosed in Applicant's International Patent Application No. PCT/US2012/030192 is preferably disposed to deposit seeds 42 from a hopper 226 into the trench 38, e.g., through a seed tube 232 disposed to guide the seeds toward the trench. In some embodiments, instead of a seed tube 232, a seed conveyor is implemented to convey seeds from the seed meter to the trench at a controlled rate of speed as disclosed in U.S. patent application Ser. No. 14/347,902 and/or U.S. Pat. No. 8,789,482. In such embodiments, a bracket is preferably configured to mount the seed firmer to the shank via sidewalls extending laterally around the seed conveyor, such that the seed firmer is disposed behind the seed conveyor to firm seeds into the soil after they are deposited by the seed conveyor. In some embodiments, the meter is powered by an electric drive 315 configured to drive a seed disc within the seed meter. In other embodiments, the drive 315 may comprise a hydraulic drive configured to drive the seed disc. A seed sensor 305 (e.g., an optical or electromagnetic seed sensor configured to generate a signal indicating passage of a seed) is preferably mounted to the seed tube 232 and disposed to send light or electromagnetic waves across the path of seeds 42. A closing system 236 including one or more closing wheels is pivotally coupled to the row unit 200 and configured to close the trench 38.

Figure 3:
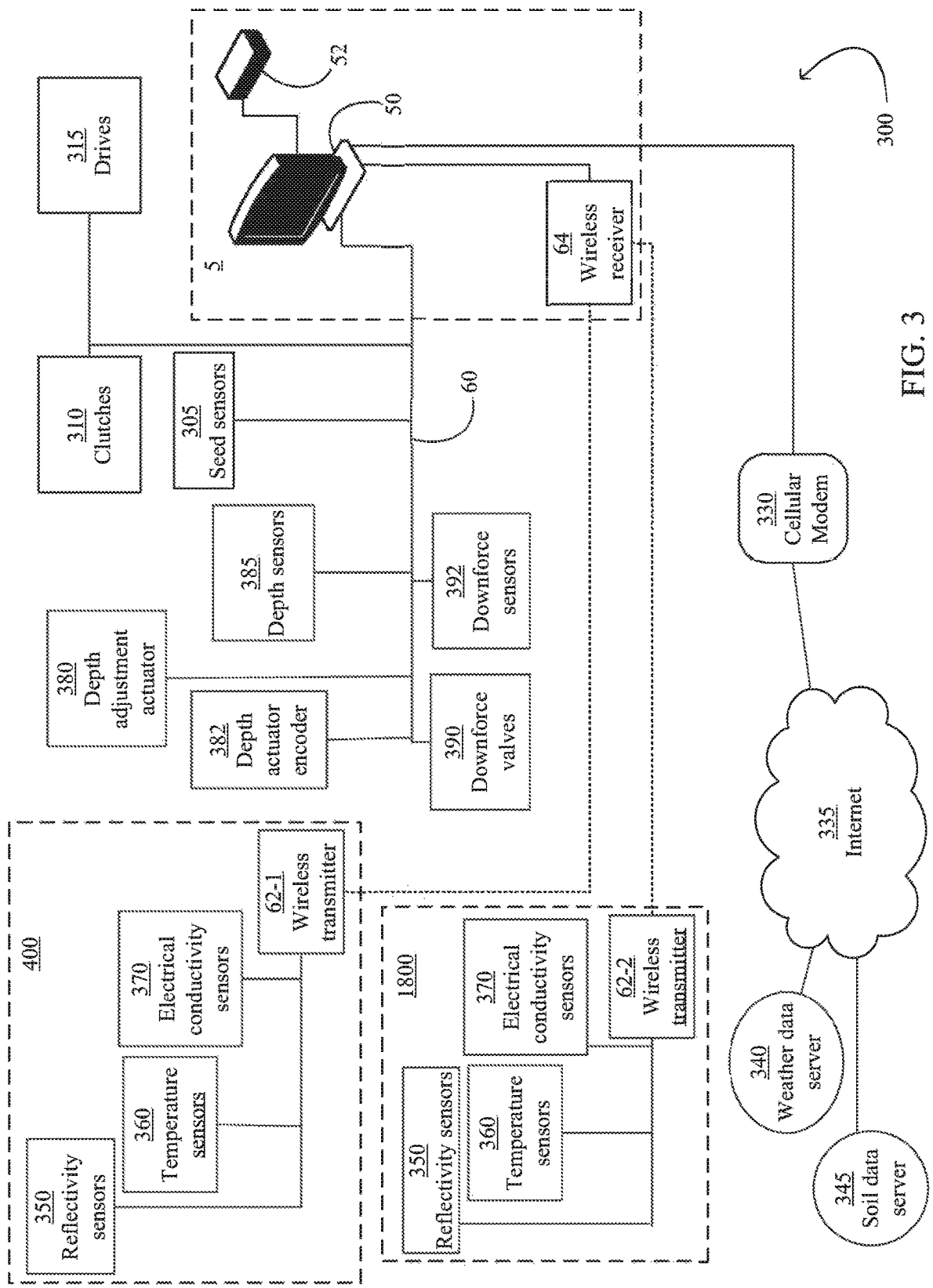
FIG. 3 schematically illustrates an embodiment of a soil monitoring system.

Turning to FIG. 3, a depth control and soil monitoring system 300 is schematically illustrated. The monitor 50 is preferably in data communication with components associated with each row unit 200 including the drives 315, the seed sensors 305, the GPS receiver 52, the downforce sensors 392, the valves 390, the depth adjustment actuator 380, and the depth actuator encoders 382. In some embodiments, particularly those in which each seed meter 230 is not driven by an individual drive 315, the monitor 50 is also preferably in data communication with clutches 310 configured to selectively operably couple the seed meter 230 to the drive 315.

Continuing to refer to FIG. 3, the monitor 50 is preferably in data communication with a cellular modem 330 or other component configured to place the monitor 50 in data communication with the Internet, indicated by reference numeral 335. The internet connection may comprise a wireless connection or a cellular connection (e.g., LTE, 5G). Via the Internet connection, the monitor 50 preferably receives data from a weather data server 340 and a soil data server 345. Via the Internet connection, the monitor 50 preferably transmits measurement data (e.g., measurements described herein) to a recommendation server (which may be the same server as the weather data server 340 and/or the soil data server 345) for storage and receives agronomic recommendations (e.g., planting recommendations such as planting depth, whether to plant, which fields to plant, which seed to plant, or which crop to plant) from a recommendation system stored on the server; in some embodiments, the recommendation system updates the planting recommendations based on the measurement data provided by the monitor 50.

Continuing to refer to FIG. 3, the monitor 50 is also preferably in data communication with one or more temperature sensors 360 mounted to the planter 10 and configured to generate a signal related to the temperature of soil being worked by the planter row units 200. The monitor 50 is preferably in data communication with one or more reflectivity sensors 350 mounted to the planter 10 and configured to generate a signal related to the reflectivity of soil being worked by the planter row units 200.

Referring to FIG. 3, the monitor 50 is preferably in data communication with one or more electrical conductivity sensors 365 mounted to the planter 10 and configured to generate a signal related to the temperature of soil being worked by the planter row units 200.

In some embodiments, a first set of reflectivity sensors 350, temperature sensors 360, and electrical conductivity sensors are mounted to a seed firmer 400 and disposed to measure reflectivity, temperature and electrical conductivity, respectively, of soil in the trench 38. In some embodiments, a second set of reflectivity sensors 350, temperature sensors 360, and electrical conductivity sensors 370 are mounted to a reference sensor assembly 1800 and disposed to measure reflectivity, temperature and electrical conductivity, respectively, of the soil, preferably at a depth different than the sensors on the seed firmer 400.

In some embodiments, a subset of the sensors are in data communication with the monitor 50 via a bus 60 (e.g., a CAN bus). In some embodiments, the sensors mounted to the seed firmer 400 and the reference sensor assembly 1800 are likewise in data communication with the monitor 50 via the bus 60. However, in the embodiment illustrated in FIG. 3, the sensors mounted to the seed firmer the sensors mounted to the seed firmer 400 and the reference sensor assembly 1800 are in data communication with the monitor 50 via a first wireless transmitter 62-1 and a second wireless transmitter 62-2, respectively. The wireless transmitters 62 at each row unit are preferably in data communication with a single wireless receiver 64 which is in turn in data communication with the monitor 50. The wireless receiver may be mounted to the toolbar 14 or in the cab of the tractor 5.

Soil Monitoring, Seed Monitoring and Seed Firming Apparatus

Figure 4A:
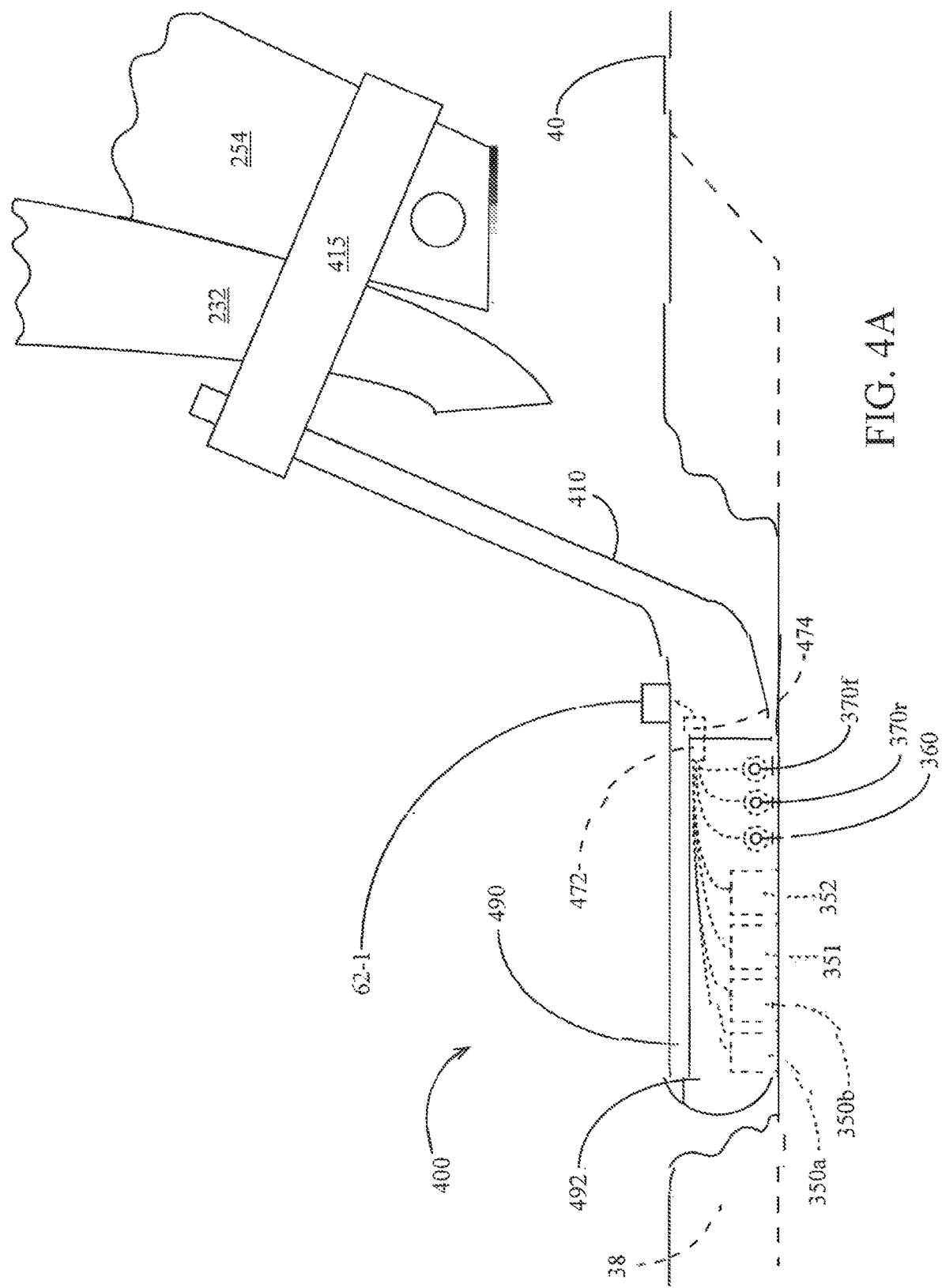
FIG. 4A is a side elevation view of an embodiment of a seed firmer having a plurality of firmer-mounted sensors.
Figure 4B:
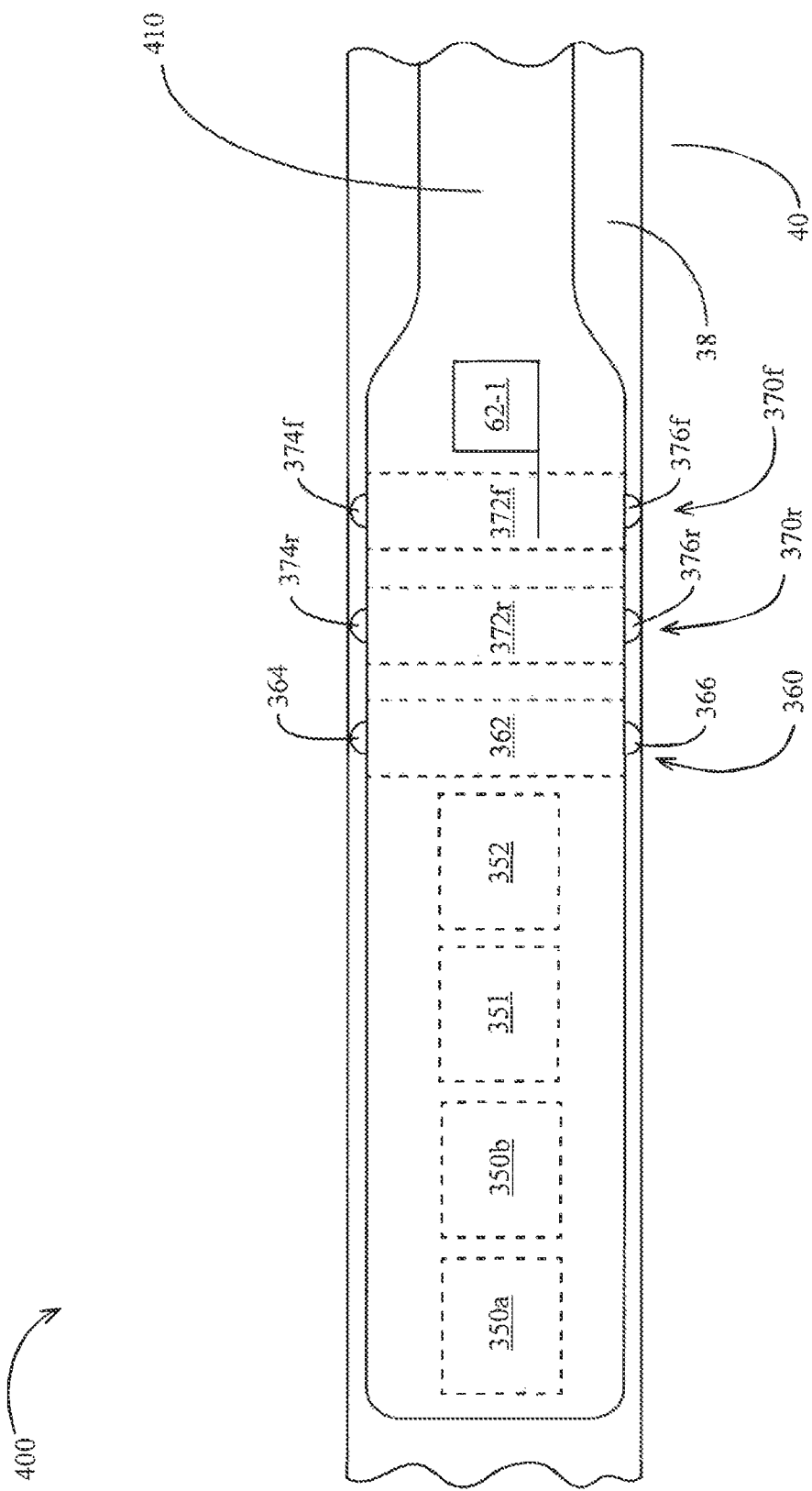
FIG. 4B is a plan view of the seed firmer of FIG. 4A.
Figure 4C:
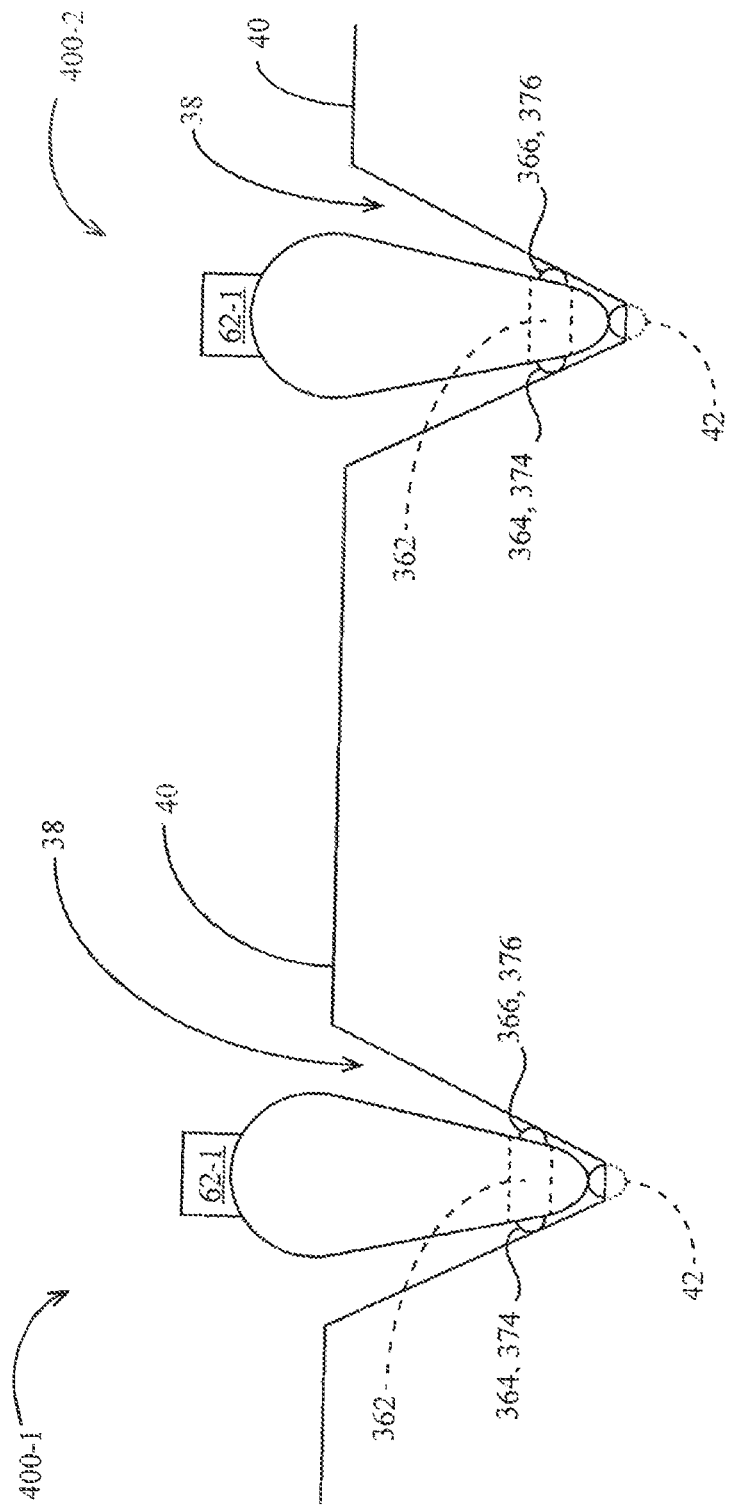
FIG. 4C is a rear elevation view of the seed firmer of FIG. 4A.

Turning to FIGS. 4A-4C, an embodiment of a seed firmer 400 is illustrated having a plurality of sensors for sensing soil characteristics. The seed firmer 400 preferably includes a flexible portion 410 mounted to the shank 254 and/or the seed tube 232 by a bracket 415. In some embodiments, the bracket 415 is similar to one of the bracket embodiments disclosed in U.S. Pat. No. 6,918,342. The seed firmer preferably includes a firmer body 490 disposed and configured to be received at least partially within v-shaped trench 38 and firm seeds 42 into the bottom of the trench. When the seed firmer 400 is lowered into the trench 38, the flexible portion 410 preferably urges the firmer body 490 into resilient engagement with the trench. In some embodiments the flexible portion 410 preferably includes an external or internal reinforcement as disclosed in PCT/US2013/066652. In some embodiments the firmer body 490 includes a removable portion 492; the removable portion 492 preferably slides into locking engagement with the remainder of the firmer body. The firmer body 490 (preferably including the portion of the firmer body engaging the soil, which in some embodiments comprises the removable portion 492) is preferably made of a material (or has an outer surface or coating) having hydrophobic and/or anti-stick properties, e.g. having a Teflon graphite coating and/or comprising a polymer having a hydrophobic material (e.g., silicone oil or polyether-ether-ketone) impregnated therein. Alternatively, the sensors can be disposed on the side of seed firmer 400 (not shown).

Returning to FIGS. 4A through 4C, the seed firmer 400 preferably includes a plurality of reflectivity sensors 350a, 350b. Each reflectivity sensor 350 is preferably disposed and configured to measure reflectivity of soil; in a preferred embodiment, the reflectivity sensor 350 is disposed to measure soil in the trench 38, and preferably at the bottom of the trench. The reflectivity sensor 350 preferably includes a lens disposed in the bottom of the firmer body 490 and disposed to engage the soil at the bottom of the trench 38. In some embodiments the reflectivity sensor 350 comprises one of the embodiments disclosed in U.S. Pat. No. 8,204,689 and/or U.S. Provisional Patent Application 61/824,975 ("the '975 application"). In various embodiments, the reflectivity sensor 350 is configured to measure reflectivity in the visible range (e.g., 400, 460, 520, 589, and/or 600 nanometers), in the near-infrared range (e.g., 850, 940 nanometers) and/or elsewhere the infrared range.

The seed firmer 400 may also include a capacitive moisture sensor 351 disposed and configured to measure capacitance moisture of the soil in the seed trench 38, and preferably at the bottom of trench 38.

The seed firmer 400 may also include an electronic tensiometer sensor 352 disposed and configured to measure soil moisture tension of the soil in the seed trench 38, and preferably at the bottom of trench 38.

Alternatively, soil moisture tension can be extrapolated from capacitive moisture measurements or from reflectivity measurements (such as at 1450 nm). This can be done using a soil water characteristic curve based on the soil type.

The seed firmer 400 may also include a temperature sensor 360. The temperature sensor 360 is preferably disposed and configured to measure temperature of soil; in a preferred embodiment, the temperature sensor is disposed to measure soil in the trench 38, preferably at or adjacent the bottom of the trench 38. The temperature sensor 360 preferably includes soil-engaging ears 364, 366 disposed to slidingly engage each side of the trench 38 as the planter traverses the field. The ears 364, 366 preferably engage the trench 38 at or adjacent to the bottom of the trench. The ears 364, 366 are preferably made of a thermally conductive material such as copper. The ears 364 are preferably fixed to and in thermal communication with a central portion 362 housed within the firmer body 490. The central portion 362 preferably comprises a thermally conductive material such as copper; in some embodiments the central portion 362 comprises a hollow copper rod. The central portion 362 is preferably in thermal communication with a thermocouple fixed to the central portion. In other embodiments, the temperature sensor 360 may comprise a non-contact temperature sensor such as an infrared thermometer. In some embodiments, other measurements made by the system 300 (e.g., reflectivity measurements, electrical conductivity measurements, and/or measurements derived from those measurements) are temperature-compensated using the temperature measurement made by the temperature sensor 360. The adjustment of the temperature-compensated measurement based on temperature is preferably carried out by consulting an empirical look-up table relating the temperature-compensated measurement to soil temperature. For example, the reflectivity measurement at a near-infrared wavelength may be increased (or in some examples, reduced) by 1% for every 1 degree Celsius in soil temperature above 10 degrees Celsius.

The seed firmer preferably includes a plurality of electrical conductivity sensors 370r, 370f. Each electrical conductivity sensor 370 is preferably disposed and configured to measure electrical conductivity of soil; in a preferred embodiment, the electrical conductivity sensor is disposed to measure electrical conductivity of soil in the trench 38, preferably at or adjacent the bottom of the trench 38. The electrical conductivity sensor 370 preferably includes soil-engaging ears 374, 376 disposed to slidingly engage each side of the trench 38 as the planter traverses the field. The ears 374, 376 preferably engage the trench 38 at or adjacent to the bottom of the trench. The ears 374, 376 are preferably made of an electrically conductive material such as copper. The ears 374 are preferably fixed to and in electrical communication with a central portion 372 housed within the firmer body 490. The central portion 372 preferably comprises an electrically conductive material such as copper; in some embodiments the central portion 372 comprises a copper rod. The central portion 372 is preferably in electrical communication with an electrical lead fixed to the central portion. The electrical conductivity sensor can measure the electrical conductivity within a trench by measuring the electrical current between soil-engaging ears 374 and 376.

Referring to FIG. 4B, in some embodiments the system 300 measures electrical conductivity of soil adjacent the trench 38 by measuring an electrical potential between the forward electrical conductivity sensor 370f and the rearward electrical conductivity sensor 370f. In other embodiments, the electrical conductivity sensors 370f, 370r may be disposed in longitudinally spaced relation on the bottom of the seed firmer in order to measure electrical conductivity at the bottom of the seed trench.

In other embodiments, the electrical conductivity sensors 370 comprise one or more ground-working or ground-contacting devices (e.g., discs or shanks) that contact the soil and are preferably electrically isolated from one another or from another voltage reference. The voltage potential between the sensors 370 or other voltage reference is preferably measured by the system 300. The voltage potential or another electrical conductivity value derived from the voltage potential is preferably and reported to the operator. The electrical conductivity value may also be associated with the GPS-reported position and used to generate a map of the spatial variation in electrical conductivity throughout the field. In some such embodiments, the electrical conductivity sensors may comprise one or more opening discs of a planter row unit, row cleaner wheels of a planter row unit, ground-contacting shanks of a planter, ground-contacting shoes depending from a planter shank, shanks of a tillage tool, or discs of a tillage tool. In some embodiments a first electrical conductivity sensor may comprise a component (e.g., disc or shank) of a first agricultural row unit while a second electrical conductivity sensor comprises a component (e.g., disc or shank) of a second agricultural row unit, such that electrical conductivity of soil extending transversely between the first and second row units is measured. It should be appreciated that at least one of the electrical conductivity sensors described herein is preferably electrically isolated from the other sensor or voltage reference. In one example, the electrical conductivity sensor is mounted to an implement (e.g., to the planter row unit or tillage tool) by being first mounted to an electrically insulating component (e.g., a component made from an electrically insulating material such as polyethylene, polyvinyl chloride, or a rubber-like polymer) which is in turn mounted to the implement.

Referring to FIG. 4C, in some embodiments the system 300 measures electrical conductivity of soil between two row units 200 having a first seed firmer 400-1 and a second seed firmer 400-2, respectively, by measuring an electrical potential between an electrical conductivity sensor on the first seed firmer 400-1 and an electrical conductivity sensor on the second seed firmer 400-2. In some such embodiments, the electrical conductivity sensor 370 may comprise a larger ground-engaging electrode (e.g., a seed firmer housing) comprised of metal or other conductive material. It should be appreciated that any of the electrical conductivity sensors described herein may measure conductivity by any of the following combinations: (1) between a first probe on a ground-engaging row unit component (e.g., on a seed firmer, a row cleaner wheel, an opening disc, a shoe, a shank, a frog, a coulter, or a closing wheel) and a second probe on the same ground-engaging row unit component of the same row unit; (2) between a first probe on a first ground-engaging row unit component (e.g., on a seed firmer, a row cleaner wheel, an opening disc, a shoe, a shank, a frog, a coulter, or a closing wheel) and a second probe on a second ground-engaging row unit component (e.g., on a seed firmer, a row cleaner wheel, an opening disc, a shoe, a shank, a frog, a coulter, or a closing wheel) of the same row unit; or (3) between a first probe on a first ground-engaging row unit component (e.g., on a seed firmer, a row cleaner wheel, an opening disc, a shoe, a shank, a frog, a coulter, or a closing wheel) on a first row unit and a second probe on a second ground-engaging row unit component (e.g., on a seed firmer, a row cleaner wheel, an opening disc, a shoe, a shank, a frog, a coulter, or a closing wheel) on a second row unit. Either or both of the row units described in combinations 1 through 3 above may comprise a planting row unit or another row unit (e.g., a tillage row unit or a dedicated measurement row unit) which may be mounted forward or rearward of the toolbar.

The reflectivity sensors 350, the temperature sensors 360, 360', 360", and the electrical conductivity sensors 370 (collectively, the "firmer-mounted sensors") are preferably in data communication with the monitor 50. In some embodiments, the firmer-mounted sensors are in data communication with the monitor 50 via a transceiver (e.g., a CAN transceiver) and the bus 60. In other embodiments, the firmer-mounted sensors are in data communication with the monitor 50 via wireless transmitter 62-1 (preferably mounted to the seed firmer) and wireless receiver 64. In some embodiments, the firmer-mounted sensors are in electrical communication with the wireless transmitter 62-1 (or the transceiver) via a multi-pin connector comprising a male coupler 472 and a female coupler 474. In firmer body embodiments having a removable portion 492, the male coupler 472 is preferably mounted to the removable portion and the female coupler 474 is preferably mounted to the remainder of the firmer body 190; the couplers 472, 474 are preferably disposed such that the couplers engage electrically as the removable portion is slidingly mounted to the firmer body.

Figure 5B:
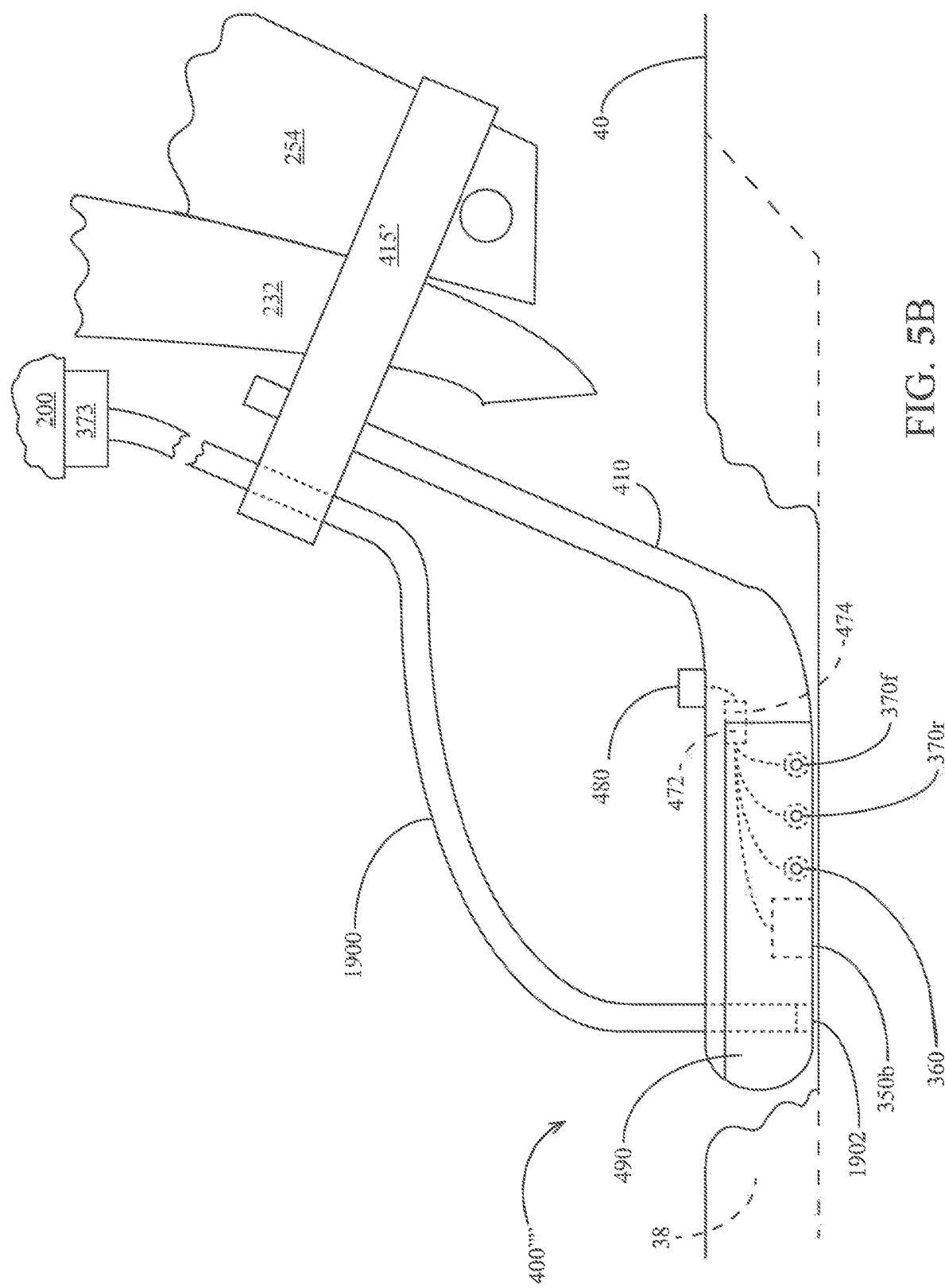
FIG. 5B illustrates a seed firmer embodiment 400'''' having a fiber-optic cable extends to a spectrometer 373 configured to analyze light transmitted from the soil.

Turning to FIG. 5A, another embodiment of the seed firmer 400''' is illustrated incorporating a fiber-optic cable 1900. The fiber-optic cable 1900 preferably terminates at a lens 1902 in the bottom of the firmer 400'''. The fiber-optic cable 1900 preferably extends to a reflectivity sensor 350a, which is preferably mounted separately from the seed firmer, e.g., elsewhere on the row unit 200. In operation, light reflected from the soil (preferably the bottom of trench 28) travels to the reflectivity sensor 350a via the fiber-optic cable 1900 such that the reflectivity sensor 350a is enabled to measure reflectivity of the soil at a location remote from the seed firmer 400'''. In other embodiments such as the seed firmer embodiment 400'''' illustrated in FIG. 5B, the fiber-optic cable extends to a spectrometer 373 configured to analyze light transmitted from the soil. The spectrometer 373 is preferably configured to analyze reflectivity at a spectrum of wavelengths. The spectrometer 373 is preferably in data communication with the monitor 50. The spectrometer 373 preferably comprises a fiber-optic spectrometer such as model no. USB4000 available from Ocean Optics, Inc. in Dunedin, Florida. In the embodiments 400''' and 400'''', a modified firmer bracket 415' is preferably configured to secure the fiber-optic cable 1900.

In certain embodiments, the wavelength used in reflectivity sensor 350 is in a range of 400 to 1600 nm. In another embodiment, the wavelength is 550 to 1450 nm. In one embodiment, there is a combination of wavelengths. In one embodiment, sensor 350 has a combination of 574 nm, 850 nm, 940 nm, and 1450 nm. In another embodiment, sensor 350 has a combination of 589 nm, 850 nm, 940 nm, and 1450 nm. In another embodiment, sensor 350 has a combination of 640 nm, 850 nm, 940 nm, and 1450 nm. In another embodiment, the 850 nm wavelength in any of the previous embodiments is replaced with 1200 nm. In another embodiment, the 574 nm wavelength of any of the previous embodiments is replaced with 590 nm. For each of the wavelengths described herein, it is to be understood that the number is actually +/−10 nm of the listed value. In certain embodiments, the combination of wavelengths is 460 nm, 589 nm, 850 nm, 1200 nm, and 1450 nm is used.

In one embodiment, the field of view from the front 402-f of lens 402' to the soil surface is 0 to 7.5 mm (0 to 0.3 inches). In another embodiment, the field of view is 0 to 6.25 mm (0 to 0.25 inches). In another embodiment, the field of view is 0 to 5 mm (0 to 0.2 inches). In another embodiment, the field of is 0 to 2.5 mm (0 to 0.1 inches).

As seed firmer 400' travels across trench 38, there may be instances where there is a gap between trench 38 and seed firmer 400' such that ambient light will be detected by reflectivity sensor 350. This will give a falsely high result. In one embodiment to remove the signal increase from ambient light, emitter 350-e can be pulsed on and off. The background signal is measured when there is no signal from emitter 350-e. The measured reflectivity is then determined by subtracting the background signal from the raw signal when emitter 350-e is emitting to provide the actual amount of reflectivity.

Figure 6A:
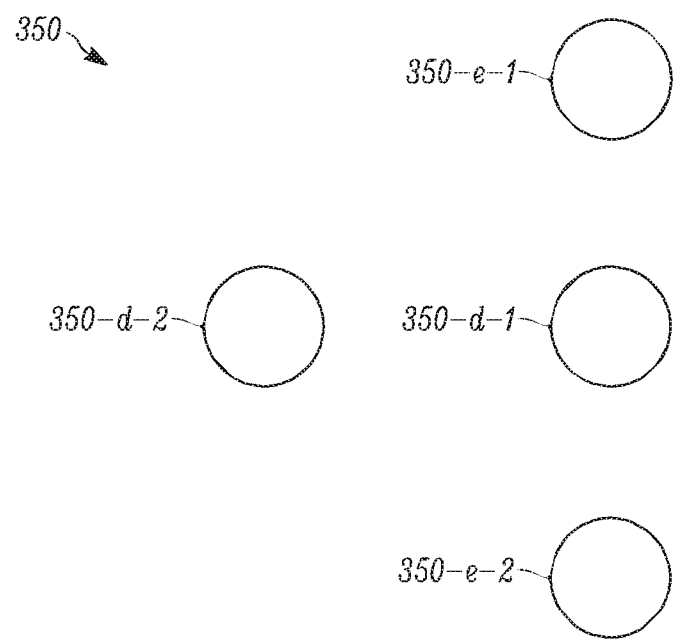
FIG. 6A is a front schematic view of a sensor with two emitters and one detector in line and an offset detector according to one embodiment.
Figure 6B:
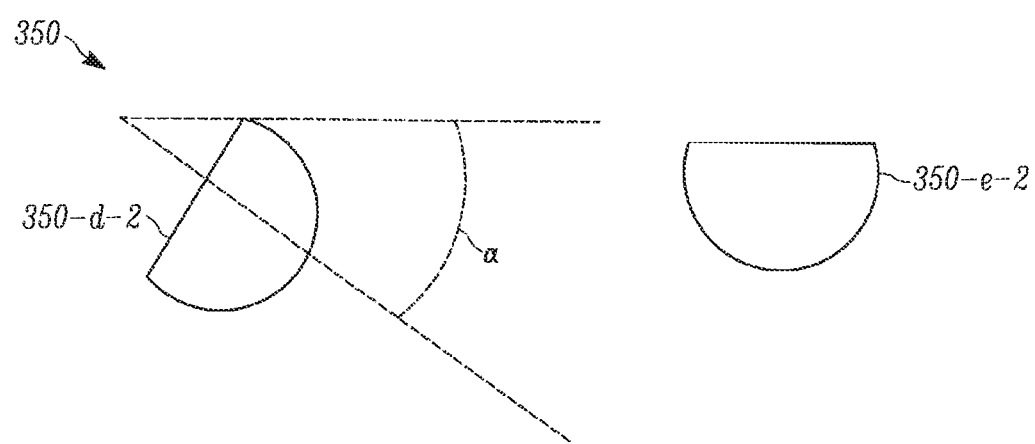
FIG. 6B is a side schematic view of the sensor of FIG. 6A.

In another embodiment as illustrated in FIGS. 6A and 6B, there is a reflectivity sensor 350 that has two emitters 350-*e*-1 and 350-*e*-2 in line with a detector 350-*d*-1. As viewed the emitters 350-*e*-1 and 350-*e*-2 are pointed out of the paper, and the view of detector 350-*d*-1 is pointed out of the paper. There is a second detector that is offset from emitters 350-*e*-1 and 350-*e*-2 and detector 350-*d*-1. In another embodiment (not shown) emitter 350-*e*-2 is omitted. As seen in FIG. 6B, detector 350-*d*-2 is angled from vertical by an angle α and is viewing towards emitters 350-*e*-1 and 350-*e*-2 and detector 350-*d*-1, which are aligned into the paper. In one embodiment, the angle α is 30 to 60°. In another embodiment, the angle α is 45°. In one embodiment, the wavelength of light used in this arrangement is 940 nm. This arrangement allows for measurement of void spaces in soil. Detecting void spaces in soil will inform how effective tillage has been. The less or smaller void spaces indicates more compaction and less effective tillage. More or larger void spaces indicates better tillage. Having this measurement of tillage effectiveness allows for adjustment of downforce on row unit 200 as described herein.

Residue coverage and soil color can be obtained from imagery. Imagery can be obtained from a satellite or an aircraft, such as a drone, or from a camera disposed over the field, such as on a pole. For user input of seed shape/size or cold germ, a user can input this information directly, a user can scan a code (bar code or QR code from a package), or a user can input the specific type of seed (or scan a code), and then the size, shape, and cold germ can be referenced from a database based on the seed type. The reference source for topography can be from stored information, such as a map, that was previously measured. Any method of measuring topography can be used. As an alternative to adjusting depth, downforce can be adjusted to effect a change in depth, or row cleaner aggressiveness can be changed.

Figure 7:
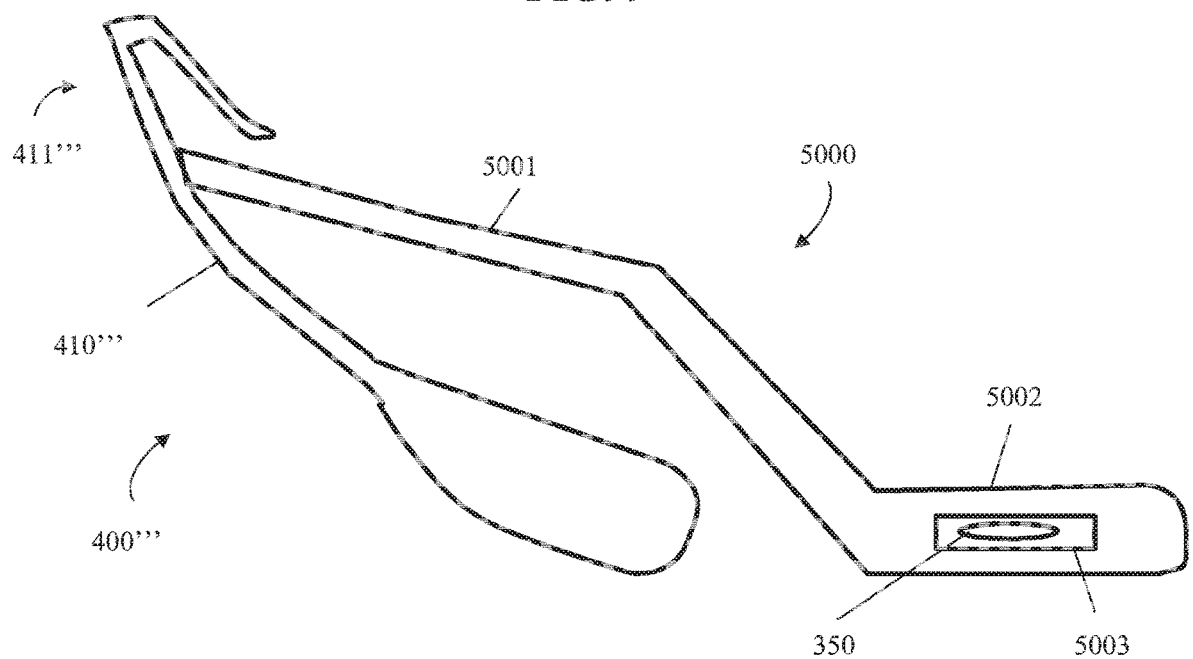
FIG. 7 is a side view of a seed firmer and sensor arm according to one embodiment.

In another embodiment, any of the previous embodiments can be in a device separate from seed firmer 400, 400'. As illustrated in FIG. 7, any of the sensors described herein (sensor 350 is illustrated in the FIG. 7) is disposed in sensor arm 5000. Sensor arm 5000 has flexible portion 5001 that is attached to seed firmer 400''' at an end of flexible portion 410''' of seed firmer 400''' proximate to bracket insert portion 411''. At the opposite end of flexible portion 5001 is base 5002. Sensor 350 is disposed in base 5002 behind lens 5003. While it is desirable for any of the sensors to be in seed firmer 400''', there may be times when a difference in the applied force is needed. In one embodiment, seed firmer 400''' may need a lower amount of force to firm a seed but a greater force is needed to keep the sensor in soil contact. A different amount of stiffness can be designed into flexible portion 5001 as compared to flexible portion 410''. By having the seed firmed by seed firmer 400, 400' first, then the biasing from sensor arm 5000 does not touch the seed that is already firmed into trench 38 or does not move the seed if contact is made.

In other embodiments, any of the sensors do not need to be disposed in a firmer. The sensors can be in any implement that is disposed on an agricultural implement in contact with the soil. For example, firmer body 490 can be mounted to any bracket and disposed anywhere on an agricultural implement and in contact with soil. Examples of an agricultural implement include, but are not limited to, planters, harvesters, sprayers, side dress bars, tillers, fertilizer spreaders, and tractor.

Figure 8:
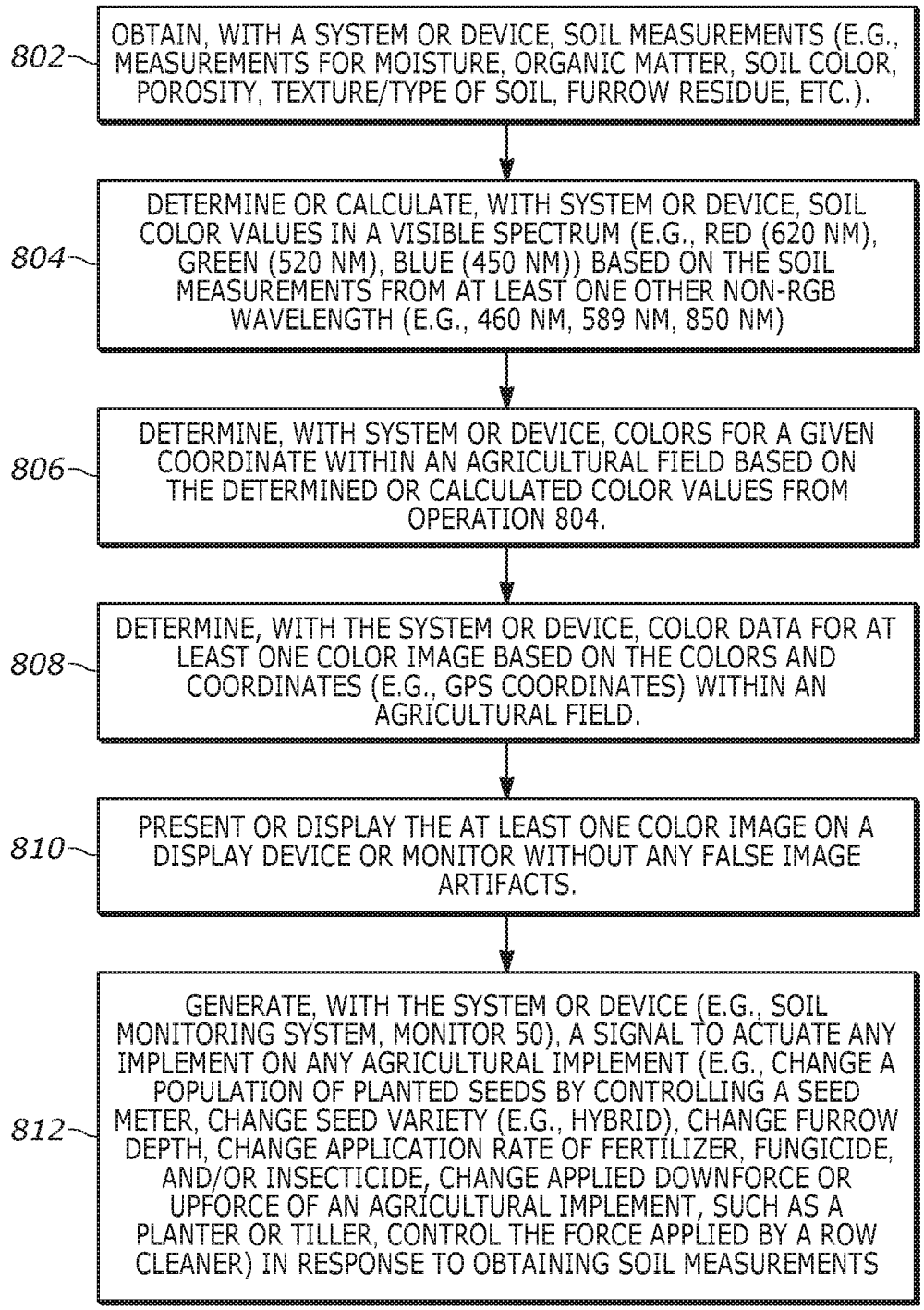
FIG. 8 illustrates a flow diagram of one embodiment for a method 800 of obtaining soil measurements and then calculating color values of the soil based on the soil measurements according to one embodiment.

FIG. 8 illustrates a flow diagram of one embodiment for a method 800 of obtaining soil measurements and then calculating color values of the soil based on the soil measurements according to one embodiment. The method 800 is performed by hardware (circuitry, dedicated logic, etc.), software (such as is run on a general purpose computer system or a dedicated machine or a device), or a combination of both. In one embodiment, the method 800 is performed by at least one system or device (e.g., monitor 50, soil monitoring system, seed firmer, sensors, implement, row unit, etc). The system or device can be local with respect to the measuring of the soil measurements or remotely located (e.g., cloud based system or device) with respect to the measuring of the soil measurements. The system executes instructions of a software application or program with processing logic. The software application or program can be initiated by a system or may notify an operator or user of a machine (e.g., tractor, planter, combine) depending on whether soil measurements cause a signal to actuate an implement.

In any embodiment herein, at operation 802, a system or device (e.g., soil monitoring system, monitor 50, seed firmer, sensors) can obtain soil measurements (e.g., measurements for moisture, organic matter, soil color, porosity, texture/type of soil, furrow residue, etc.).

At operation 804, the system or device determines or calculates soil color values in a visible spectrum (e.g., red (620 nm), green (520 nm), blue (450 nm)) based on the soil measurements from at least one other non-RGB wavelength (e.g., 460 nm, 589 nm, 850 nm). In one example, blue values are calculated based on the 460 nm wavelength. Green values are calculated based on the 460 nm wavelength and 589 nm wavelength for yellow. Red values are calculated based on the 460 nm wavelength, the 589 nm wavelength for yellow, and the 850 nm wavelength for IRA. In this example, red, green, and blue wavelengths are not measured by a soil device or apparatus. Rather, emitters and detectors for other wavelengths measure soil characteristics (e.g., measurements for moisture, organic matter, porosity, texture/type of soil, furrow residue, etc.) during an agricultural input and measurements for these other wavelengths are used to calculate red, green, and blue values for the soil. The soil device or apparatus does not need red, green, and blue sensors with emitters and detectors. In a specific example, the selected wavelengths of the soil device or apparatus measure moisture and organic matter.

At operation 806, the system or device determines colors for a given coordinate within an agricultural field based on the determined or calculated color values from operation 804.

At operation 808, the system or device determines color data for at least one color image based on the colors and coordinates (e.g., GPS coordinates) within an agricultural field.

At operation 810, the system or device presents the at least one color image on a display device or monitor without any false image artifacts.

At operation 812, the system or device (e.g., soil monitoring system, monitor 50) can optionally generate a signal to actuate any implement on any agricultural implement (e.g., change a population of planted seeds by controlling a seed meter, change seed variety (e.g., hybrid), change furrow depth, change application rate of fertilizer, fungicide, and/or insecticide, change applied downforce or upforce of an agricultural implement, such as a planter or tiller, control the force applied by a row cleaner) in response to obtaining soil measurements. This can be done in real time on the go.

Examples of soil measurements that can be measured and the control of implements include, but are not limited to:

A) moisture, organic matter, porosity, or texture/type of soil to change a population of planted seeds by controlling a seed meter;

B) moisture, organic matter, porosity, or texture/type of soil to change seed variety (e.g., hybrid);
C) moisture, organic matter, porosity, or texture/type of soil to change furrow depth;
D) moisture, organic matter, porosity, or texture/type of soil to change application rate of fertilizer, fungicide, and/or insecticide;
E) moisture, organic matter, porosity, or texture/type of soil to change applied downforce or upforce of an agricultural implement, such as a planter or tiller;
F) furrow residue to control the force applied by a row cleaner.

In one embodiment for downforce or upforce, a combination of moisture and texture/type can be used. Higher downforce can be applied in sandy and/or wet soils, and lower downforce can be used in clay and/or wet soils. Too much downforce for a given soil type can cause compaction of the soil, which decreases the ability of roots to spread throughout the soil. Too little downforce for a given soil type can allow an implement to ride up and not plant seeds to a targeted depth. The downforce is generally applied through the gauge wheels 248 adjacent to the trench.

Figure 9A:
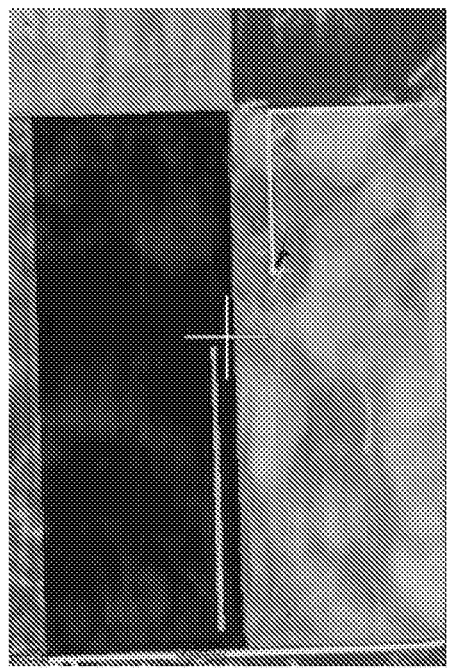
FIG. 9A illustrates an image that is generated based on calculated color values of the soil in accordance with one embodiment.
Figure 9B:
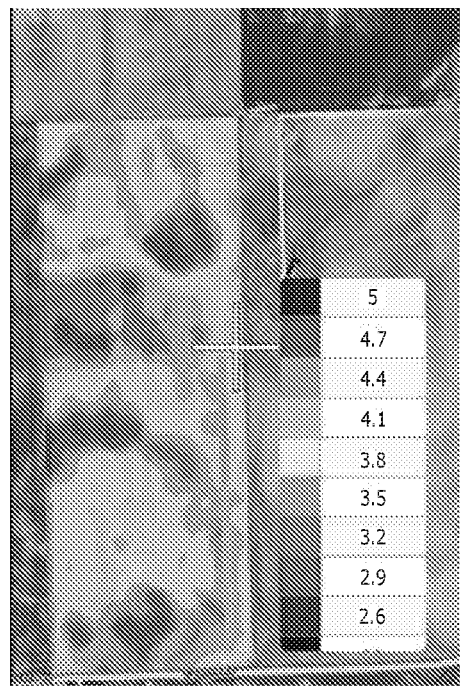
FIG. 9B illustrates an image of calculated soil metrics (i.e. Organic matter) based on the measured reflectance of one or more wavelengths.

FIG. 9B illustrates a color image that is generated based on calculated color values of the soil in accordance with one embodiment. The visible spectrum color values are added onto a field that is illustrated in FIG. 9A based on coordinates for respective color values. The color values are calculated based on measurements of reflective sensors at planting depth of soil. The color images generated can be a supplement for satellite images, but looking just under the surface of soil within a field. Additionally, the color images are generated from a sequence of subsurface soil color measurements, without any false image artifacts typically associated with satellite soil imagery such as topograpy, cover vegetation, shadows, lighting conditions, weather conditions, etc.

Figure 10:
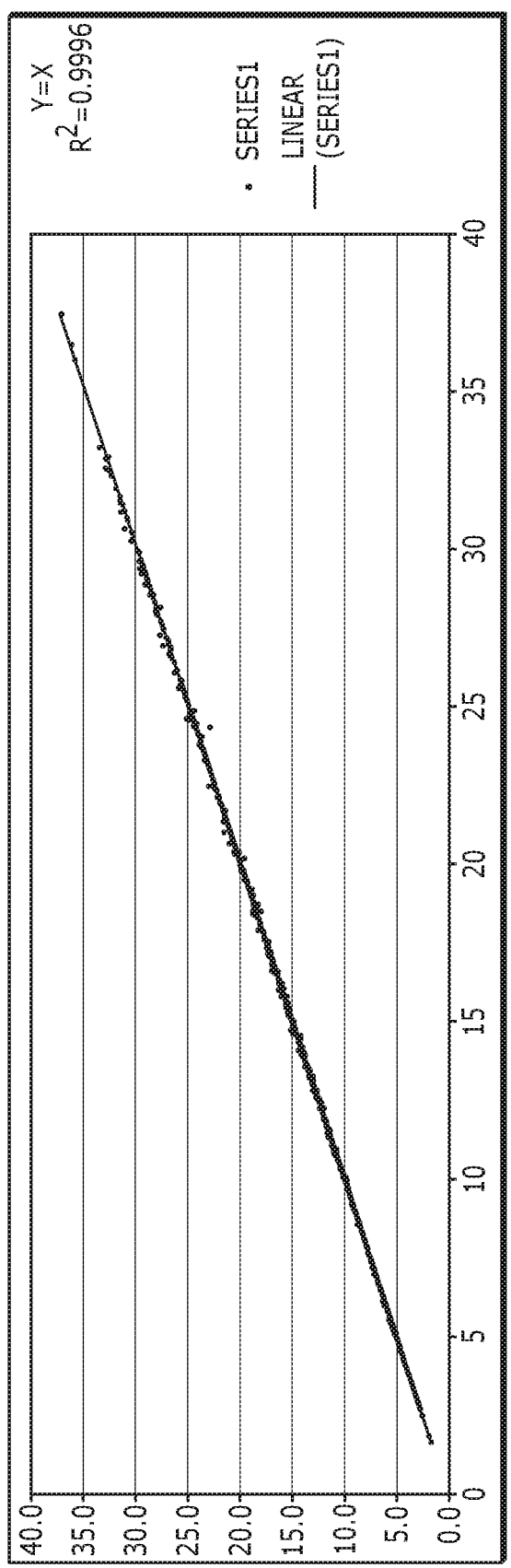
FIG. 10 illustrates a calculated RGB values correlation in accordance with one embodiment.

In one example, RGB values are obtained from an agricultural soil device or apparatus (e.g., smart seed firmer) having sensors for emitting and detecting 460 nm, 589 nm, and 850 nm wavelengths. Coefficients can be determined empirically from values in a soil library or database with 99+% R2 fit of actual RGB values as illustrated in FIG. 10. Red, green, and blue values can be determined from reflectance sensors of a soil apparatus (e.g., smart seed firmer) as follows for one example.

True_Color_Red=soil apparatus_460 nm_reflectance*(−0.209)+soil apparatus_589 nm_reflectance*1.06+soil apparatus_850 nm_reflectance*0.113

True_Color_Green=soil apparatus_460 nm_reflectance*0.789+soil apparatus_589 nm_reflectance*0.305

True_Color_Blue=soil apparatus_460 nm_reflectance

Any data that is measured during a pass through the field can be stored in a geo-referenced map and used again during a later pass in the same field during the same season or in a subsequent year. For example, organic matter can be measured during a planting pass through the field during planting. Having the geo-referenced organic matter content can be used during a fertilization pass to variable rate fertilizer based on location specific organic matter content. The data collected can be stored in a separate data file or as part of the field file.

Figure 11:
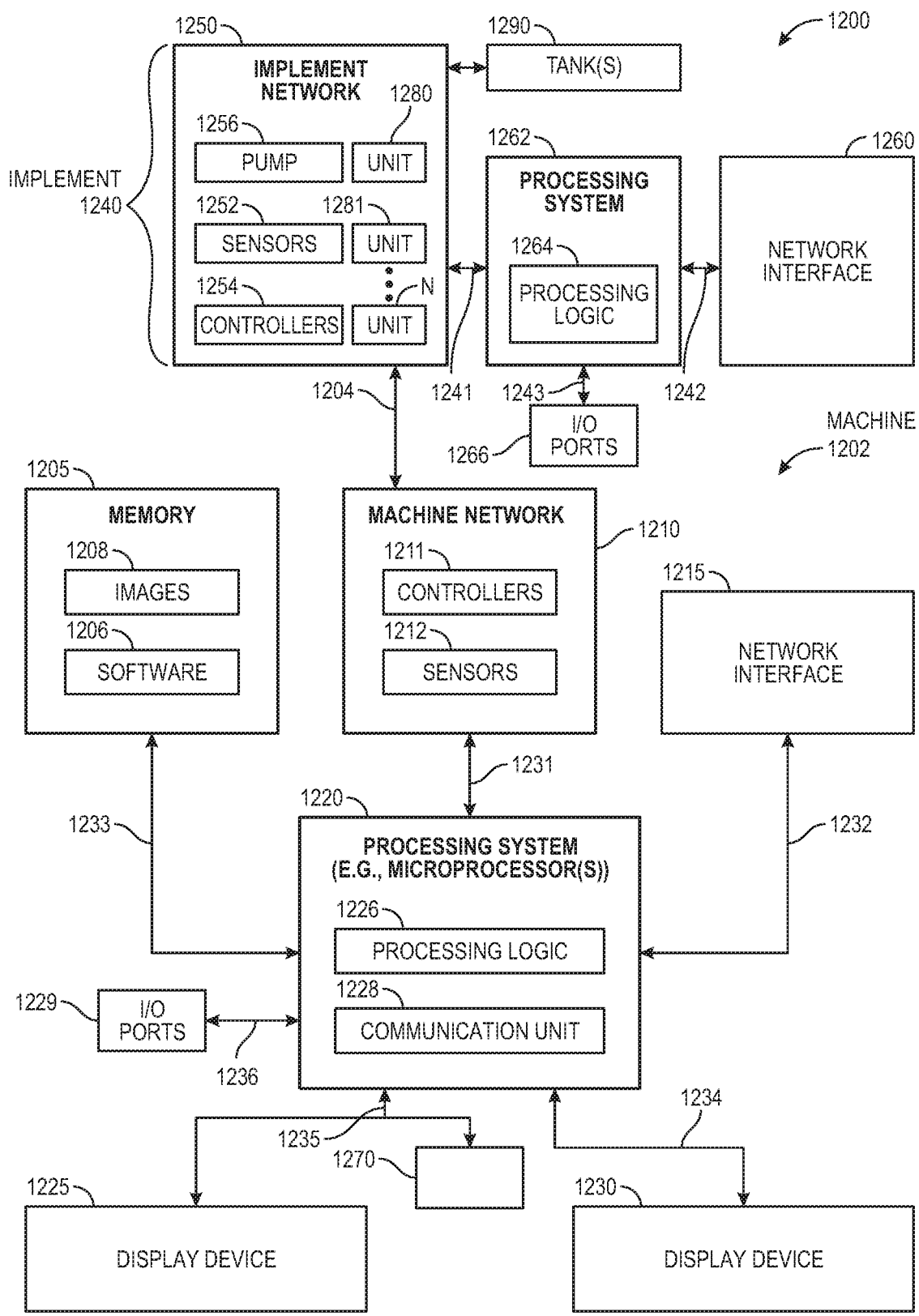
FIG. 11 shows an example of a system 1200 that includes a machine 1202 (e.g., tractor, combine harvester, etc.) and an implement 1240 (e.g., planter, sidedress bar, cultivator, plough, sprayer, spreader, irrigation implement, etc.) in accordance with one embodiment.

FIG. 11 shows an example of a system 1200 that includes a machine 1202 (e.g., tractor, combine harvester, etc.) and an implement 1240 (e.g., planter, sidedress bar, cultivator, plough, sprayer, spreader, irrigation implement, etc.) in accordance with one embodiment. The machine 1202 includes a processing system 1220, memory 1205, machine network 1210 (e.g., a controller area network (CAN) serial bus protocol network, an ISOBUS network, etc.), and a network interface 1215 for communicating with other systems or devices including the implement 1240. The machine network 1210 includes sensors 1212 (e.g., speed sensors), controllers 1211 (e.g., GPS receiver, radar unit) for controlling and monitoring operations of the machine or implement. The network interface 1215 can include at least one of a GPS transceiver, a WLAN transceiver (e.g., WiFi), an infrared transceiver, a Bluetooth transceiver, Ethernet, or other interfaces from communications with other devices and systems including the implement 1240. The network interface 1215 may be integrated with the machine network 1210 or separate from the machine network 1210 as illustrated in FIG. 12. The I/O ports 1229 (e.g., diagnostic/on board diagnostic (OBD) port) enable communication with another data processing system or device (e.g., display devices, sensors, etc.).

In one example, the machine performs operations of a tractor that is coupled to an implement for planting applications of a field. The planting data for each row unit of the implement can be associated with locational data at time of application to have a better understanding of the planting for each row and region of a field. Data associated with the planting applications can be displayed on at least one of the display devices 1225 and 1230. The display devices can be integrated with other components (e.g., processing system 1220, memory 1205, etc.) to form the monitor 50.

The processing system 1220 may include one or more microprocessors, processors, a system on a chip (integrated circuit), or one or more microcontrollers. The processing system includes processing logic 1226 for executing software instructions of one or more programs and a communication unit 1228 (e.g., transmitter, transceiver) for transmitting and receiving communications from the machine via machine network 1210 or network interface 1215 or implement via implement network 1250 or network interface 1260. The communication unit 1228 may be integrated with the processing system or separate from the processing system. In one embodiment, the communication unit 1228 is in data communication with the machine network 1210 and implement network 1250 via a diagnostic/OBD port of the I/O ports 1229.

Processing logic 1226 including one or more processors or processing units may process the communications received from the communication unit 1228 including agricultural data (e.g., GPS data, planting application data, soil characteristics, any data sensed from sensors of the implement 1240 and machine 1202, etc.). The processing logic 1226 can process soil measurements to determine soil color values. The system 1200 includes memory 1205 for storing data and programs for execution (software 1206) by the processing system. The memory 1205 can store, for example, software components such as planting application software for analysis of soil and planting applications for performing operations of the present disclosure, or any other software application or module, images (e.g., captured images of crops, soil, furrow, soil clods, row units, etc.), alerts, maps, etc. The memory 1205 can be any known form of a machine readable non-transitory storage medium, such as semiconductor memory (e.g., flash; SRAM; DRAM; etc.) or non-volatile memory, such as hard disks or solid-state drive. The system can also include an audio input/output subsystem (not shown) which may include a microphone and a speaker for, for example, receiving and sending voice commands or for user authentication or authorization (e.g., biometrics).

The processing system 1220 communicates bi-directionally with memory 1205, machine network 1210, network interface 1215, header 1280, display device 1230, display device 1225, and I/O ports 1229 via communication links 1231-1236, respectively. The processing system 1220 can be integrated with the memory 1205 or separate from the memory 1205.

Display devices 1225 and 1230 can provide visual user interfaces for a user or operator. The display devices may include display controllers. In one embodiment, the display device 1225 is a portable tablet device or computing device with a touchscreen that displays data (e.g., planting application data, captured images, localized view map layer, soil color data and images, high definition field maps of seed germination data, seed environment data, as-planted or as-harvested data or other agricultural variables or parameters, yield maps, alerts, etc.) and data generated by an agricultural data analysis software application and receives input from the user or operator for an exploded view of a region of a field, monitoring and controlling field operations. The operations may include configuration of the machine or implement, reporting of data, control of the machine or implement including sensors and controllers, and storage of the data generated. The display device 1230 may be a display (e.g., display provided by an original equipment manufacturer (OEM)) that displays images and data for a localized view map layer, as-applied fluid application data, as-planted or as-harvested data, yield data, seed germination data, seed environment data, controlling a machine (e.g., planter, tractor, combine, sprayer, etc.), steering the machine, and monitoring the machine or an implement (e.g., planter, combine, sprayer, etc.) that is connected to the machine with sensors and controllers located on the machine or implement.

A cab control module 1270 may include an additional control module for enabling or disabling certain components or devices of the machine or implement. For example, if the user or operator is not able to control the machine or implement using one or more of the display devices, then the cab control module may include switches to shut down or turn off components or devices of the machine or implement.

The implement 1240 (e.g., planter, cultivator, plough, sprayer, spreader, irrigation implement, etc.) includes an implement network 1250, a processing system 1262, a network interface 1260, and optional input/output ports 1266 for communicating with other systems or devices including the machine 1202. The implement network 1250 (e.g, a controller area network (CAN) serial bus protocol network, an ISOBUS network, etc.) includes a pump 1256 for pumping fluid from a storage tank(s) 1290 to application units 1280, 1281, . . . N of the implement, sensors 1252 (e.g., speed sensors, seed sensors for detecting passage of seed, sensors for detecting characteristics of soil or a trench including soil moisture, soil organic matter, soil temperature, soil color, seed presence, seed spacing, percentage of seeds firmed, and soil residue presence, downforce sensors, actuator valves, moisture sensors or flow sensors for a combine, speed sensors for the machine, seed force sensors for a planter, fluid application sensors for a sprayer, or vacuum, lift, lower sensors for an implement, flow sensors, etc.), controllers 1254 (e.g., GPS receiver), and the processing system 1262 for controlling and monitoring operations of the implement. The pump controls and monitors the application of the fluid to crops or soil as applied by the implement. The fluid application can be applied at any stage of crop development including within a planting trench upon planting of seeds, adjacent to a planting trench in a separate trench, or in a region that is nearby to the planting region (e.g., between rows of corn or soybeans) having seeds or crop growth.

For example, the controllers may include processors in communication with a plurality of seed sensors. The processors are configured to process data (e.g., fluid application data, seed sensor data, soil data, furrow or trench data) and transmit processed data to the processing system 1262 or 1220. The controllers and sensors may be used for monitoring motors and drives on a planter including a variable rate drive system for changing plant populations. The controllers and sensors may also provide swath control to shut off individual rows or sections of the planter. The sensors and controllers may sense changes in an electric motor that controls each row of a planter individually. These sensors and controllers may sense seed delivery speeds in a seed tube for each row of a planter.

The network interface 1260 can be a GPS transceiver, a WLAN transceiver (e.g., WiFi), an infrared transceiver, a Bluetooth transceiver, Ethernet, or other interfaces from communications with other devices and systems including the machine 1202. The network interface 1260 may be integrated with the implement network 1250 or separate from the implement network 1250 as illustrated in FIG. 12.

The processing system 1262 communicates bi-directionally with the implement network 1250, network interface 1260, and I/O ports 1266 via communication links 1241-1243, respectively.

The implement communicates with the machine via wired and possibly also wireless bi-directional communications 1204. The implement network 1250 may communicate directly with the machine network 1210 or via the networks interfaces 1215 and 1260. The implement may also by physically coupled to the machine for agricultural operations (e.g., planting, harvesting, spraying, etc.).

The memory 1205 may be a machine-accessible non-transitory medium on which is stored one or more sets of instructions (e.g., software 1206) embodying any one or more of the methodologies or functions described herein. The software 1206 may also reside, completely or at least partially, within the memory 1205 and/or within the processing system 1220 during execution thereof by the system 1200, the memory and the processing system also constituting machine-accessible storage media. The software 1206 may further be transmitted or received over a network via the network interface 1215.

In one embodiment, a machine-accessible non-transitory medium (e.g., memory 1205) contains executable computer program instructions which when executed by a data processing system cause the system to performs operations or methods of the present disclosure. While the machine-accessible non-transitory medium (e.g., memory 1205) is shown in an exemplary embodiment to be a single medium, the term "machine-accessible non-transitory medium" should be taken to include a single medium or multiple media (e.g., a centralized or distributed database, and/or associated caches and servers) that store the one or more sets of instructions. The term "machine-accessible non-transitory medium" shall also be taken to include any medium that is capable of storing, encoding or carrying a set of instructions for execution by the machine and that cause the machine to perform any one or more of the methodologies of the present disclosure. The term "machine-accessible non-transitory medium" shall accordingly be taken to include, but not be limited to, solid-state memories, optical and magnetic media, and carrier wave signals.

Any of the following examples can be combined into a single embodiment or these examples can be separate embodiments. In one example of a first embodiment, a method of calculating soil color data includes obtaining, with sensors of a soil apparatus, soil measurements including at least one of measurements for moisture, organic matter, porosity, type of soil, and furrow residue. The method further includes calculating soil color values in a visible spectrum including at least one of red, green, and blue color values based on the soil measurements and determining color data for at least one color image without false image artifacts based on the calculated soil color values and associated coordinates within an agricultural field.

What is claimed is:

1. A method of calculating soil color data, the method comprising:
   obtaining, with sensors of a soil apparatus that emit and detect one or more of non-red (R) green (G) blue (B) wavelengths of light, a sequence of subsurface soil color measurements including at least one of measurements for moisture, organic matter, porosity, type of soil, or furrow residue during an agricultural input of an agricultural implement having the soil apparatus;
   calculating, with processing logic, soil color values in a visible light spectrum including at least one of red, green, and blue color values based on the soil color measurements from the one or more non-RGB wavelengths of light; and
   determining color data for at least one color image without false image artifacts based on the calculated soil color values and associated coordinates within an agricultural field.

2. The method of claim 1, further comprising:
   presenting the at least one color image on a display device or monitor without any false image artifacts.

3. The method of claim 1, wherein the soil measurements are obtained without measuring at least one of red, green, and blue wavelengths of light.

4. The method of claim 1, wherein the blue color values are calculated based on measuring a 460 nm wavelength of light.

5. The method of claim 1, wherein the green color values are calculated based on measuring a 460 nm wavelength of light and measuring a 589 nm wavelength of light for yellow.

6. The method of claim 1, wherein the red color values are calculated based on measuring a 460 nm wavelength of light, measuring a 589 nm wavelength of light for yellow, and measuring a 850 nm wavelength of light.

7. The method of claim 1, further comprising:
   generating a signal in real time during an agricultural operation to actuate any implement on any agricultural implement in response to obtaining soil measurements.

8. The method of claim 7, wherein the actuation of any implement causes one or more of a change in a population of planted seeds by controlling a seed meter, a change in seed variety, a change in furrow depth, a change in application rate of fertilizer, fungicide, and/or insecticide, or a change in applied downforce or upforce of an agricultural implement in response to obtaining soil measurements.

9. The method of claim 1, wherein the soil apparatus comprises a seed firmer to obtain soil measurements including at least one of measurements for moisture, organic matter, porosity, type of soil, and furrow residue.

10. The method of claim 1, wherein the sensors comprise reflective sensors positioned on an implement at a planting depth of soil.

11. A system for monitoring soil characteristics, the system comprising:
   sensors to emit and detect one or more of non-red (R) green (G) blue (B) wavelengths of light to obtain subsurface soil color measurements including at least one of measurements for moisture, organic matter, porosity, type of soil, or furrow residue during an agricultural input of an agricultural implement;
   a communication unit to receive data including the soil color measurements sensed from the sensors of the agricultural implement; and
   processing logic coupled to the communication unit, wherein the processing logic is configured to receive the soil color measurements including at least one of measurements for moisture, organic matter, porosity, type of soil, or furrow residue,
   to calculate soil color values in a visible light spectrum including at least one of red, green, and blue color values based on the received soil color measurements from the one or more non-RGB wavelengths of light, and
   to determine color data for at least one color image without false image artifacts based on the calculated soil color values and associated coordinates within an agricultural field.

12. The system of claim 11, wherein the processing logic is further configured to send the at least one color image to a display device or monitor.

13. The system of claim 11, wherein the soil measurements are obtained without measuring at least one of red, green, and blue wavelengths of light.

14. The system of claim 11, wherein the blue color values are calculated based on measuring a 460 nm wavelength of light.

15. The system of claim 11, wherein the green color values are calculated based on measuring a 460 nm wavelength of light and measuring a 589 nm wavelength of light for yellow.

16. The system of claim 11, wherein the red color values are calculated based on measuring a 460 nm wavelength of light, measuring a 589 nm wavelength of light for yellow, and measuring a 850 nm wavelength of light.

17. The system of claim 11, wherein the processing logic is further configured to generate a signal in real time during an agricultural operation to cause actuation of any implement on any agricultural implement in response to obtaining soil measurements.

18. The system of claim 17, wherein the actuation of any implement causes one or more of a change in a population of planted seeds by controlling a seed meter, a change in seed variety, a change in furrow depth, a change in application rate of fertilizer, fungicide, and/or insecticide, or a change in applied downforce or upforce of an agricultural implement in response to obtaining soil measurements.

19. The system of claim 11, wherein the soil measurements are obtained from sensors of a seed firmer of the agricultural implement.

20. The system of claim 11, wherein the sensors comprise reflective sensors positioned on the agricultural implement at a planting depth of soil.

* * * * *